United States Patent
Chandler et al.

(10) Patent No.: US 6,649,414 B1
(45) Date of Patent: *Nov. 18, 2003

(54) MICROPARTICLES WITH MULTIPLE FLUORESCENT SIGNALS AND METHODS OF USING SAME

(75) Inventors: Mark B. Chandler, Austin, TX (US); Don J. Chandler, Austin, TX (US)

(73) Assignee: Luminex Corporation, Austin, TX (US)

( * ) Notice: Subject to any disclaimer, the term of this patent is extended or adjusted under 35 U.S.C. 154(b) by 111 days.

This patent is subject to a terminal disclaimer.

(21) Appl. No.: 09/639,818

(22) Filed: Aug. 17, 2000

Related U.S. Application Data

(60) Provisional application No. 60/149,225, filed on Aug. 17, 1999.

(51) Int. Cl.[7] .................. G01N 33/48; G01N 33/536
(52) U.S. Cl. .................. 436/63; 436/8; 436/19; 436/164; 436/166; 436/172; 436/805; 436/808; 436/823; 436/518; 436/523; 436/534; 435/6; 435/7.1; 435/810; 435/975; 422/61
(58) Field of Search .................. 436/8, 19, 63, 436/164, 166, 172, 800, 805, 808, 823, 501, 518, 523, 533, 534; 435/7.1, 810, 4, 6, 7.2, 975; 422/61

(56) References Cited

U.S. PATENT DOCUMENTS

| | | | | |
|---|---|---|---|---|
| 4,279,617 A | * | 7/1981 | Masson et al. ............ 422/57 |
| 4,774,189 A | * | 9/1988 | Schwartz .................. 436/10 |
| 4,987,539 A | | 1/1991 | Moore et al. | |
| 5,073,498 A | * | 12/1991 | Schwartz et al. ............ 435/967 |
| 5,093,234 A | * | 3/1992 | Schwartz .................... 356/213 |
| 5,194,300 A | * | 3/1993 | Cheung .................. 252/301.35 |
| 5,326,692 A | * | 7/1994 | Brinkley et al. ........ 252/301.34 |
| 5,567,627 A | * | 10/1996 | Lehnen .................... 435/973 |
| 5,641,634 A | * | 6/1997 | Mandecki .................. 340/10.3 |
| 5,736,330 A | * | 4/1998 | Fulton ...................... 435/210 |
| 5,747,349 A | * | 5/1998 | van den Engh et al. .... 356/246 |
| 5,759,793 A | * | 6/1998 | Schwartz et al. ........... 210/660 |
| 5,786,219 A | * | 7/1998 | Zhang et al. ............ 422/82.07 |
| 5,872,015 A | | 2/1999 | Venton et al. | |
| 5,981,180 A | * | 11/1999 | Chandler et al. .............. 435/6 |
| 6,043,066 A | * | 3/2000 | Mangano et al. ......... 435/173.1 |
| 6,268,222 B1 | * | 7/2001 | Chandler et al. ........... 435/174 |

OTHER PUBLICATIONS

Phan, Quang N., International Search Report For PCT/US99/01315, Apr. 7, 1999.
Zinngrebe, U. International Search Report for PCT/US00/22543, Oct. 25, 2000.

* cited by examiner

*Primary Examiner*—Maureen M. Wallenhorst
(74) *Attorney, Agent, or Firm*—Gilberto M. Villacorta; Robert R. Seabold; Katten Muchin Zavis Rosenman

(57) ABSTRACT

This invention provides a novel fluorescent particle including a core or carrier particle having on its surface a plurality of smaller polymeric particles or nanoparticles, which are stained with different fluorescent dyes. When excited by a light source they are capable of giving off multiple fluorescent emissions simultaneously, which is useful for multiplexed analysis of a plurality of analytes in a sample. The coupled complex particles carrying on their surface fluorescent nanoparticles, methods of preparing such polymer particles, and various applications and methods of using such particles are claimed.

38 Claims, No Drawings

MICROPARTICLES WITH MULTIPLE FLUORESCENT SIGNALS AND METHODS OF USING SAME

RELATED APPLICATIONS

This application claims priority from U.S. Provisional Application No. 60/149,225, filed Aug. 17, 1999, incorporated herein by reference.

FIELD OF THE INVENTION

This invention generally relates to microparticles with unique characteristics detectable by instruments and methods for use in the measurement of analytes in fluids.

BACKGROUND OF THE INVENTION

Fluorescent polymeric particles have often found utility as markers and indicators in various biomedical assays. Fluorescent particles are usually obtained by embedding or diffusing a fluorescent dye according to the technique originally described by L. B. Bangs (Uniform Latex Particles; Seragen Diagnostics Inc. 1984, p. 40). Other methods are known in the art to stain particles with fluorescent dyes. The microparticles can then be analyzed manually or by other methods known in the art, but preferably using an automated technique, e.g., flow cytometry, such as disclosed in U.S. Pat. No. 4,665,024 issued to Mansour, et al.

The versatility of these particles can be enhanced by the incorporation in a single particle of a plurality of dyes, each dye having unique spectral characteristics. One skilled in the art would recognize that two or more dyes of varying proportions could be used to increase the permutation number of unique combinations of dyes on a single particle. While simple absorption of a single dye into a particle has proven adequate for most purposes, several problems arise when more than one dye is absorbed into a particle.

First, the close proximity of embedded dye molecules gives rise to significant amounts of fluorescent energy transfer. This energy transfer leads to fluorescent emissions that are inconsistent with relative dye concentrations and their original emission patterns.

A second problem arises when the dye substances used have differing solubilities in the solvent used to incorporate the dye in the particles. Since all dyes must be absorbed simultaneously, possible dye ratios are restricted by solvent properties.

A third problem that has been encountered when multiple dyes are embedded in microparticles is the change in dye spectra. Specifically, it has been noted that, when the particle is composed of crosslinked polystyrene, a significant broadening of the fluorescent emission peak occurs. This can result in an overlapping of the spectra of neighboring dyes.

One method that may circumvent these problems is to chemically couple each dye substance to the surface of the particle. This approach is, for example, disclosed in U.S. Pat. Nos. 5,194,300 Cheung and 4,774,189 Schwartz, whereby one or several fluorescent dyes are covalently bound to the surface of particles. This, however, leaves the dye molecule exposed to the environment, which can hasten decomposition by oxidation or other chemical attack. Additionally, a large number of surface binding sites would be occupied by dye and would be unavailable for the conjugation of analytical reactant molecules necessary to perform the assays.

Hence, it is desirable to have multicolored fluorescent particles, which avoid the above problems. This invention minimizes or eliminates these complications while maintaining the versatility of multi-dye particles.

Masson et al., disclose in U.S. Pat. No. 4,279,617, latex particles of relatively large diameter (e.g. 0.79 $\mu$m) coated with an analytical reactant, e.g., allergen, either by simple adsorption or by covalent coupling with cyanogen bromide or hydroxylated latex. A sample of human serum from a person suspected to have an allergic reaction, is mixed with a suspension of these particles. The mixture is incubated and latex particles of a relatively smaller diameter (e.g. 0.08 $\mu$m) are then added. These smaller particles are coated with rabbit anti-IgE antibodies and if larger particles have IgE bound to the allergen these small particles will bind to these antibodies and will form by virtue of agglomeration reaction so-called agglutination particles, i.e., large particles surrounded by several smaller particles. However, these particles are bound to each other via non-covalent binding and the agglomeration occurs as the consequence and result of the presence of the analyte of interest. No admission is made that any reference cited in this specification is prior art. All references cited herein are hereby expressly incorporated by reference.

SUMMARY OF THE INVENTION

This invention involves microparticles which are uniquely distinguished by detectable characteristics. In addition, the microparticles have bound to them reagents which react with analytes in samples to be analyzed in bimolecular reactions. The results of the reactions are bound to the microparticles and are measured, thereby allowing quantification of the amount of analyte in each sample. A variety of instruments are used to characterize the microparticles and simultaneously measure the bimolecular reactions. These include flow cytometry, electrophoresis cells, and centrifuges.

This invention provides significant advantages and efficiencies in the analysis of clinical and other samples from a single source for a number of analytes, and for analyzing a number of samples from a variety of sources for a single analyte. Any system or instrument capable of separating microparticles into subpopulations according to specified characteristics and of determining a chemical reaction using the same detection method as for the characteristics may be used with this invention. For example, flow cytometry using fluorescence detection is the embodiment described in greatest detail below. Other suitable systems include free flow electrophoresis and centrifugation, both of which may use detection means based on fluorescence, electrical charge, impedance, magnetic properties, etc.

Accordingly, this invention provides a novel article, which comprises a polymer microparticle having attached to its surface one or more populations or sets of fluorescently stained nanoparticles. All nanospheres in a given population are dyed with the same concentration of a dye, and by coupling a predetermined number of these nanospheres to the microparticle, along with known quantities of other nanospheres stained with different dyes, a multifluorescent microsphere results. By varying the quantity and ratio of different populations or sets of nanospheres it is possible to establish and distinguish a large number of discreet populations of carrier particles with unique emission spectra or fluorescence signal.

It is an object of the invention to provide a novel article, which comprises a microparticle carrying on its surface one or more populations of fluorescently stained nanoparticles. All nanospheres in a given population are dyed with the same concentration of a dye, and by coupling a known quantity of these nanospheres to the microparticle, along with known quantities of other nanospheres stained with different dyes, a multifluorescent microsphere results. By varying the quantity and ratio of different populations of nanospheres it is possible to establish and distinguish a large number of discreet populations of carrier particles with unique emission spectra. The carrier particles can be stained as well to provide an additional color or signal.

Although the article of the invention could appear as being similar to existing agglutination particles disclosed by Masson et al., and other similar prior art disclosures, they are patentably distinct from the instant invention, because means and the sequential order of particle-to-particle coupling are radically dissimilar. The purpose of the agglutination assay and means of the detection are also drastically different. Thus the prior art disclosures relating to particle agglutination methods and compositions are totally irrelevant and unrelated to the instant invention. The article of the instant invention requires that it is formed prior to the detection of an analyte of interest.

Polymeric microparticles used in this invention as carrier or core particles have a diameter of less than one millimeter, preferably having a size ranging from about 0.1 to about 1,000 micrometers ($\mu$m) in diameter. Even though the microparticle can be of any size, the preferred size is 1–100 $\mu$m, more preferably 2–50 $\mu$m, more preferably 3–25 $\mu$m, and even more preferably about 6–12 $\mu$m.

Preferred sizes for nanoparticles range from about 1 nanometer (nm) to about 100,000 nm in diameter. Optimally preferred diameters are within about 10 and 1,000 nm, preferably within 100 and 800 nm, and more preferably within 200 and 500 nm.

It is a further object of the invention to provide nanospheres as well as carrier particles, which are preferably made of polymer material, i.e., polystyrene. However, polymeric materials including but not limited to brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosphaze, polysulfone, or combinations thereof are acceptable as well. Other polymer materials such as carbohydrate, e.g., carboxymethyl cellulose, hydroxyethyl cellulose, agar, gel, proteinaceous polymer, polypeptide, eukaryotic and prokaryotic cells, viruses, lipid, metal, resin, latex, rubber, silicone, e.g., polydimethyldiphenyl siloxane, glass, ceramic, charcoal, kaolinite, bentonite, and the like can be equally used.

These polymers may also incorporate magnet or magnetically responsive metal oxides selected from the group consisting of superparamagnetic, paramagnetic, and ferromagnetic metal oxide.

It is a still further object of this invention to provide particles which will contain about 0% to 70% (weight/weight) of a cross-linking agent, such as divinyl benzene, ethylene glycol dimethacrylate, trimethylol propane trimethacrylate, or N,N'methylene-bis-acrylamide or other functionally equivalent agents known in the art. In a preferred embodiment, core microspheres, as well as nanospheres, are made of polystyrene and contain about 0% to 30% divinyl benzene.

It is a still further object of this invention to provide particles which will contain additional surface functional groups such as carboxylates, esters, alcohols, carbamides, aldehydes, amines, sulfur oxides, nitrogen oxides, or halides, which may facilitate attachment of analytical reactants and/or particle-to-particle bonding.

It is a still further object of the invention to provide methods of preparing microparticles by covalent coupling or any other known means of coupling, e.g., ionic bonds, hydrogen bonds, or by simple adsorption. Other methods of coupling are provided, including, the coupling by an adsorption followed by surrounding the article of invention with a polymeric shell.

It is a still further object of the invention to provide dyes that are fluorescent dyes. Preferably such dyes are hydrophobic and are capable of staining polymeric particles. The preferred dyes are cyanine dyes. For specific purposes such as labeling label or detection reagents, i.e., an antibody, the hydrophilic dyes such as fluorescein (FITC) can be used.

It is a still further object of the invention to provide dyes with light emission at a wavelength in the ultra-violet or visible range. It is a still further object of the invention to provide dyes that fluoresce in the infrared or near infrared region.

It is a still further object of the invention to provide dyes with light emission at a wavelength of greater than about 450 nm, preferably greater than about 480 nm, more preferably at greater than about 500 nm. The preferred dyes are polymethine cyanines or squaraines, which emit fluorescent light having wavelengths in the region of about 500 nm to about 1000 nm. Preferably, when more than one dye is used to stain more than one population of nanospheres, these dyes are chosen such that they possess substantially different emission spectra, preferably having emission maxima separated by greater than 10 nm, more preferably having emission maxima separated by greater than 25 nm, even more preferably separated by greater than 50 nm. Dyes can be selected to have emission bands that match commercially available filters or for detecting multiple fluorophores with several excitation and emission bands.

It is a still further object of the invention to provide methods of using such particles for various diagnostic, analytic, and industrial applications known in the art. It is a still further object of the invention to provide a kit suitable for use in detection of the analytes of interest. Preferably, this kit contains a series of microparticles with attached nanoparticles having a distinct fluorescent signal and also an analytical reactant capable of specifically binding with one of analytes of interest. The kit also contains a secondary reagent comprising a reagent, which binds to the same analyte as the analytical reagent and also this kit may contain a fluorescent label, a competitor molecule, a reference material, and other ingredients that are accepted as standard reagents such as a wash buffer, necessary plasticware, etc.

It is a still further object of the invention to detect and analyze various analytes which can be in a broader sense an antigen, an antibody (both monoclonal and polyclonal), a receptor, a hapten, an enzyme, a protein, a peptide, a nucleic acid, a drug, a hormone, a chemical, a polymer, a pathogen, a toxin, or combination thereof.

It is a further object of this invention to provide methods for detecting multiple subpopulations of analytes of interest in a sample employing multicolored particles of the instant invention.

In accordance with the above and further objects of the invention, the preferred method to detect, differentiate, sort, quantitate, and/or analyze aspects or portions of analytes in a sample is by flow cytometry.

It is a further object of this invention to provide other means for detection and analysis, including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, scanning microscopes, confocal microscopes, capillary electrophoresis detectors, or by other means for amplifying the signal such as a photomultiplier tube or other light detector capable of detecting the presence, location, intensity, excitation and emission spectra, fluorescence polarization, fluorescence lifetime, and other physical properties of the fluorescent signal.

It is a further object of this invention to provide rapid and efficient methods for analyzing samples of several origins for a single analytes.

It is a further object of this invention to provide rapid and efficient methods for analyzing samples of a single origin for a variety of analytes.

DETAILS OF SPECIFIC EMBODIMENTS

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise. Thus, for example, reference to a method of staining "a particle" with "a dye" may include a mixture of one or more dyes and one or more particles. As used hereinafter the terms fluorescent dye, fluorescer, fluorochrome, or fluorophore are used interchangeably and bear equivalent meanings.

Particles

As used hereinafter the terms microparticles, microspheres, or microbeads are used interchangeably and bear equivalent meanings as they refer to small particles with overall diameter that falls essentially in the micrometer range. The terms nanospheres, nanoparticles, or nanobeads refer to smaller particles with overall size that falls essentially in the nanometer range. As used hereinafter the general term particles, spheres, or beads refers both to microparticles and nanoparticles, which effectively serve as solid supports or solid phase.

Fluorescent polymer nanospheres coupled to carrier microparticles are described. Fluorescently distinguishable particle sets are obtained through variation of the amount and type of dye in the nanospheres. The desirable number of nanospheres linked to the microparticle, and ratios of differently dyed nanospheres on the surface of the carrier particle are selected according to particular need.

Nanospheres used in this invention are commercially available in sizes ranging from about 10 nanometers (nm) to about 100,000 nm in diameter. Optimally preferred diameters are within about 10 and 1,000 nm, preferably within 200 and 500 nm. Polymeric microspheres used in this invention as carrier particles to which nanospheres are bound normally range in size from 0.01 to 1000 micrometers ($\mu$m) in diameter. Even though the microparticle can be of any size, the preferred size is 0.1–500 $\mu$m, more preferably 1–200 $\mu$m, and even more preferably 2–12 $\mu$m. The particles can be uniform (being about the same size) or of variable size such that the differences can be determined by size-dependent properties such as light scattering or optical refraction.

Particles are made of any regularly shaped material. The preferred shape is spherical, however, particles of any other shape can be employed since this parameter is immaterial to the nature of the invention. The shape of the particle can serve as an additional distinction parameter, which is discriminated by flow cytometry, e.g., by a high-resolution slit-scanning method.

Usually these nanospheres as well as carrier particles are made of the same material such as polystyrene or latex. However, other polymeric materials are acceptable including polymers selected from the chemical group consisting of carbohydrate-based polymers, polyaliphatic alcohols, poly (vinyl) polymers, polyacrylic acids, polyorganic acids, polyamino acids, co-polymers, block co-polymers, tertpolymers, polyethers, naturally occurring polymers, polyimids, surfactants, polyesters, branched polymers, cyclo-polymers, polyaldehydes and mixtures thereof. More specifically, brominated polystyrene, polyacrylic acid, polyacrylonitrile, polyamide, polyacrylamide, polyacrolein, polybutadiene, polycaprolactone, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, or combinations thereof are preferable. Representative combination polymers of which the polymeric particles are composed include for example poly-(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m&p-divinylbenzene) (89:10:1 molar ratio), poly-(styrene-co-2-carboxyethyl acrylate) (90:10 molar ratio), poly(methyl methacrylate-co-acrylic acid) (70:30 molar ratio) and poly (styrene-co-butyl acrylate-co-methacrylic acid)(45:45:10 weight ratio). Most of beads formed from synthetic polymers such as polystyrene, polyacrylamide, polyacrylate, or latex are now commercially available from numerous sources such as Bio-Rad Laboratories (Richmond, Calif.) and LKB Produkter (Stockholm, Sweden). Beads formed from natural macromolecules and particles such as agarose, crosslinked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia.

These polymers may also incorporate magnet or magnetically responsive metal oxide selected from the group consisting of superparamagnetic, paramagnetic, and ferromagnetic metal oxide. Magnetic beads are commercially available from sources such as Dynal Inc. (Great Neck, N.Y.) or can be prepared using known in the art methods as disclosed for example in U.S. Pat. Nos. 4,358,388; 4,654, 267; 4,774,265; 5,320,944; and 5,356,713.

Other materials such as carbohydrate, e.g., carboxymethyl cellulose, hydroxyethyl cellulose, proteinaceous polymer, polypeptide, eukaryotic and prokaryotic cells, viruses, lipid, metal, resin, rubber, silica, silicone, e.g., polydimethyldiphenyl siloxane, glass, ceramic and the like can be equally used.

The nanoparticles are preferably made of the same material as the microparticles. However, if required, they can be made of different material. It is to be understood that in this Specification the terms "first" and "second", as applied to polymer species which compose microparticles and nanoparticles are used for the purposes of identification only and do not imply any order of preference.

The microspheres will also contain approximately 0% to 70% of a cross-linking agent, such as divinyl benzene, ethylene glycol dimethacrylate, trimethylol propane trimethacrylate, or N,N'methylene-bis-acrylamide or other functionally equivalent agents known in the art. Crosslinking of carbohydrate polymer such as hydroxypropyl cellulose can be achieved with adipic acid, sebacic acid, succinic acid, citric acid, 1,2,3,4-butanetetracarboxylic acid, or 1,10 decanedicarboxylic acid. In a preferred embodiment, core microspheres and nanospheres are made of polystyrene and contain about 0% to 30% divinyl benzene.

The particles may have additional surface functional groups to facilitate the attachment and bonding. These groups may include carboxylates, esters, alcohols, carbamides, aldehydes, amines, sulfur oxides, nitrogen oxides, or halides. Carboxylated latex particles have been used to prepare diagnostic reagents as described, for example, in U.S. Pat. No. 4,181,636. As described therein, the conventional procedure for covalently attaching an immunologically reactive species to the particles having surface carboxyl groups involves the use of a water-soluble carbodiimide. For many practical applications it is critical that the polymeric particles have surface carboxyl groups available for attachment of the reactive amine- or sulfhydryl-containing compound. Such groups are preferably added to the particles by incorporating monomers containing such groups into the polymers (for example, acrylic acid, methacrylic acid, itaconic acid, and the like). Alternatively, they can be added to the particles by further chemical reaction of a polymer having other precursor reactive groups which can be converted to carboxyl groups (for example, by hydrolysis of anhydrides, such as maleic anhydride, or by oxidation of surface methylol or aldehyde end groups). Other compounds, such as diamines, dihydrazides, mercaptoalkylamines and dimercaptans can be used as linking moieties for later attachment of drugs, enzymes or other reactive species such as nanospheres. Although the preferred attaching or bonding method is by covalent linkage, other methods such as adsorption can be equally used. Other novel methods such as surrounding microparticle-nanoparticle complexes by a polymeric shell are acceptable as well.

Dyes

Fluorescent dyes used in this invention are preferebly of the general class known as cyanine dyes, with emission wavelengths between 550 nm and 900 nm. These dyes may contain methine groups and their number influences the spectral properties of the dye. The monomethine dyes that are pyridines typically have blue to blue-green fluorescence emission, while quinolines have green to yellow-green fluorescence emission. The trimethine dye analogs are substantially shifted toward red wavelengths, and the pentamethine dyes are shifted even further, often exhibiting infrared fluorescence emission (see, for example, U.S. Pat. No. 5,760,201).

However, any dye that is soluble in an organic solvent can be used. The squaric acid based fluorescent dyes can be synthesized by methods described in the literature. See, for example, Sprenger et al. Angew. Chem., 79, 581 (1967); Angew. Chem., 80, 541 (1968); and Maaks et al., Angew Chem. Intern. Edit., 5, 888 (1966). Additionally, unsymmetrically substituted squaric acid compounds can be synthesized by methods such as those described by Law et al., J. Org. Chem. 57, 3278, (1992). Specific methods of making some of such dyes are well known in the art and can be found for example in U.S. Pat. Nos. 5,795,981; 5,656,750; 5,492,795; 4,677,045; 5,237,498; and 5,354,873. The practical use of above the described fluorescent dyes, e.g., phthalocyanines, 2,3-naphthalocyanines, squaraines and croconic acid derivatives is disclosed in U.S. Pat. No. 5,525,516 issued to Krutak, et al.

In addition to fluorescent dyes used in this preferred embodiment, related dyes can be further selected from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm. In addition to squaraines, i.e., derived from squaric acid, hydrophobic dyes such as phthalocyanines and naphthalocyanines can also be selected to operate at longer wavelengths. Other classes of fluorochromes are equally suitable for use as dyes according to the present invention. Some of these dyes are listed herein: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroaryl-substituted Polyolefin, Astrazon Brilliant Red 4 G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH-CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. Optionally such dyes will contain functional groups capable of forming a stable fluorescent product with functional groups typically found in biomolecules or polymers including activated esters, isothiocyanates, amines, hydrazines, halides, acids, azides, maleimides, alcohols, acrylamides, haloacetamides, phenols, thiols, acids, aldehydes and ketones.

One skilled in the art would know which one to select among such dyes as long as the desired emission and absorption properties as well as their hydrophobic properties are appropriate. The spectral properties of the fluorescent dyes should be sufficiently similar in excitation wavelengths and intensity to fluorescein or rhodamine derivatives as to permit the use of the same flow cytometry equipment. It is preferable that the dyes, however, have higher solubility in organic solvents and have improved photostability and quantum yields.

More preferably, the dyes have the same or overlapping excitation spectra, but possess distinguishable emission spectra. Any detection system can be used to detect the difference in spectral characteristics between the two dyes, including a solid state detector, photomultiplier tube, photographic film, or eye, any of which may be used in conjunction with additional instrumentation such as a spectrometer, luminometer microscope, plate reader, fluorescent scanner, flow cytometer, or any combination thereof, to complete the detection system. Preferably dyes are chosen such that they possess substantially different emission spectra, preferably having emission maxima separated by greater than 10 nm, more preferably having emission maxima separated by greater than 25 nm, even more preferably separated by greater than 50 nm. When differentiation between the two dyes is accomplished by visual inspection, the two dyes preferably have emission wavelengths of perceptibly different colors to enhance visual discrimination. When it is desirable to differentiate between the two dyes using instrumental methods, a variety of filters and diffraction gratings allow the respective emission maxima to be independently detected. When two dyes are selected that possess similar emission maxima, instrumental discrimination can be enhanced by insuring that both dyes' emission spectra have similar integrated amplitudes, similar bandwidths, and the instrumental system's optical throughput be equivalent across the emission range of the two dyes. Instrumental discrimination can also be enhanced by selecting dyes with narrow bandwidths rather than broad bandwidths, however such dyes must necessarily possess a high amplitude emission or be present in sufficient concentration that the loss of integrated signal strength is not detrimental to signal detection.

Staining Process

The technology is available enabling one skilled in the art to make a series of multicolored, fluorescent particles with unique fluorescence characteristics and using such particles for multiparameter analysis of a plurality of analytes. According to this technology, both microparticles and nanoparticles can be subjected to fluorescent staining with distinct dyes. In the preferred embodiment, the nanoparticles are stained and more preferably more than one set of nanoparticles are provided which are stained with one or more distinct fluorescent dyes. Fluorescent staining of polymeric particles may be achieved by any of the techniques familiar to those skilled in the art. Three distinct means of making fluorescent particles are known, including: (i) covalent attachment of dyes onto the surface of the particle, (ii) internal incorporation of dyes during particle polymerization, and (iii) dyeing after the particle has already been polymerized.

(i) U.S. Pat. Nos. 5,194,300 Cheung and 4,774,189 Schwartz, disclose, for example, fluorescent microspheres that are coated by covalently attaching to their surface one or more fluorescent dyes.

(ii) U.S. Pat. Nos. 5,073,498 Schwartz and 4,717,655 Fulwyler, disclose fluorescent dyes added during particle polymerization process.

(iii) The principle of the third method, i.e., internally embedding or diffusing a dye after a particle has been already polymerized was originally described by L.B.Bangs (Uniform Latex Particles; Seragen Diagnostics Inc. 1984, p. 40). U.S. Pat. No. 5,723,218 issued to Haugland et al. discloses diffusely dyeing microparticles with one or more dipyrromethene boron difluoride dyes by using a process, which is essentially similar to the Bangs method. The combination of above methods are also possible and these examples are offered by way of illustration and not by way of limitation. One such technique is described here:

A 1% w/w solution of nanospheres (300 nm diameter polystyrene, amino functionalized) is stirred in a round bottom flask. To this is added a solution of the dye in an organic solvent, such as chloroform. When the dye solution is no longer absorbed by the nanospheres, addition of the dye is halted and the solvent is removed under reduced pressure.

In another embodiment, two fluorescent dyes are used, e.g., red squaraine dye which is 1,3-bis [(1,3-dihydro- 1,3, 3-trimethyl-2H-indol-2-ylidene)methyl]-2,4-dihydroxy-cyclobutenediylium, bis(inner salt) and orange squaraine dye is 2-(3,5-dimethylpyrrol-2-yl)-4-(3,5-dimethyl-2H-pyrrol-2-ylidene)-3-hydroxy- 2-cyclobuten 1-one. These dyes are used to stain two separate populations of nanospheres. Alternatively, one population of nanospheres and carrier microsphere are stained. As another alternative, two dyes are combined at different ratio within the same particle of a given population.

Optimal staining with a particular dye is dependent upon the physical and chemical nature of the individual dye or polymeric substrate and the dye medium, as well as the property being assessed. Incubation times may vary widely depending on the desirable results, the concentration of the dye and the particles and the reaction conditions. The optimal time is usually the minimum time required for the dye, in the concentration being used, to achieve the highest specific signal while avoiding degradation of the dye over time and minimizing all other undesirable fluorescent signals due to the dye.

The total dye quantity is between about 0.00001% and 15% by weight to particle weight. This limitation, is however, of little consequence to the present invention for as long as the particle impregnated with said dyes is stable and usable for its intended purpose.

Both dyes would preferably be excited at the same absorption wavelength, e.g., ranging from ultraviolet to about 800 nm, and emit fluorescent light at two distinct, essentially non-overlapping wavelengths distant from each other by at least 10 nm, preferably 30 nm, and more preferably by at least 50 nm. For example, the emission peak of the first dye may be at 585 nm, and the peak emission of the second dye may be at 630 nm.

Alternatively, the dye of the invention is selected to give a detectable response that is different from that of other reagents desired to be used in combination with the subject dyes. For example, dyes that form complexes that permit excitation beyond 600 nm can be used in combination with commonly used fluorescent antibodies such as those labeled with fluorescein isothiocyanate or phycoerythrin.

Any fluorescence detection system (including visual inspection) can be used to detect differences in spectral properties between dyes, with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof. The detectably different dye is optionally one of the dyes of the invention having different spectral properties and different selectivity. In one aspect of the invention, the dye-particle complex and the additional detection reagents have the same or overlapping excitation spectra, but possess visibly different emission spectra, generally having emission maxima separated by >10 nm, preferably >20 nm, more preferably >50 nm. Simultaneous excitation of all fluorescent reagents may require excitation of the sample at a wavelength that is suboptimal for each reagent individually, but optimal for the combination of reagents. Alternatively, the additional reagent(s) can be simultaneously or sequentially excited at a wavelength that is different from that used to excite the subject dye. In yet another alternative, one or more additional reagents are used to quench or partially quench dye emission.

In a preferred embodiment, chlorinated solvents, more preferably chloroform, are used to solubilize dyes. However, suitable solvents are selected based on their ability to solubilize the particular class of hydrophobic dyes of interest. The solvents can be acyl, aliphatic, cycloaliphatic, aromatic or heterocyclic hydrocarbons; the solvents may or may not have halogens, oxygen, sulfur, nitrogen, and/or phosphorus as either terminal groups or as integral parts of a ring or chain. Specifically, solvents such as alcohol, ethyl acetate, toluene, xylene, hexane, pentane, benzene, ether, acetone, oil, carbone tetrachloride, carbon disulfide, DMSO, or methylene chloride can be used. Other solvents known in the art can be used and may be selected among various solvents listed in the Merck Index (Eleventh Edition, see section MISC-63–68).

The resulting dyed nanospheres may then be linked to the dyed or undyed microparticles by any of the well-known coupling reactions such as carbodiimide coupling (see below). Other methods of coupling using carboxylates, esters, alcohols, carbamides, aldehydes, amines, sulfur oxides, nitrogen oxides, or halides can be used as well by methods well known in the art.

Methods of Using the Article of Invention

The present invention provides a fluorescent polymeric article, comprising a carrier microparticle carrying one or more nanoparticles with multiple fluorescent signals.

Optionally, the carrier microparticle of the invention can be also stained with a distinct fluorescent dye. To obtain such an article, a carrier particle is coated (covalently or by adsorption) with a plurality of smaller fluorescent particles (nanoparticles) with an average size from about 100 to 500 nanometers in diameter regardless of shape and composition. The article can be further coated or surrounded by a thin polymeric shell, selected in such a way that it would not affect light absorption and emission characteristics. This is accomplished by either of two separate methods described hereinafter.

The fluorescent nanoparticles of this invention may be prepared by incorporating either a single fluorescent dye and combining one or more populations of nanoparticles at different ratios. Alternatively, a combination of two or more fluorescent dyes within the same particle can be used to obtain multifluorescent nanoparticles. The fluorescence intensity of these fluorescent nanoparticles can be adjusted by varying the amount of fluorescent dye incorporated. The surface of both types of particles can be modified further to provide the desired surface characteristics allowing attachment of functional groups or chemical bonds.

In addition to flow cytometry, calibration purposes the fluorescent particles having these characteristics are useful in a wide variety of biomedical applications. The analytical method is also provided which is based on using multicolored fluorescent microparticles obtained by the instant invention. When each such population of microparticles, characterized by at least two fluorescent signals, is combined with an analytical reactant capable of binding a specific analyte of interest in a clinical or test sample a powerful analytical tool is obtained, which can provide qualitative and quantitative assay results. To achieve truly multiplexed analysis of a plurality of analytes in a sample, a third type of fluorescent signal, e.g., green fluorescent signal (FITC) is provided, usually found in a label reagent, which is capable of binding the analyte of interest. The label reagent as defined herein thus has two functions: the capacity to react with the analyte and the capacity to provide a fluorescent signal, which is distinct from the fluorescence signal of the particle of the invention. An ordinary flow cytometer is capable of analyzing spectral properties (fluorescent signals) of up to 20,000 particles per second and can provide reliable quantitative data in real-time scale. Thus, methods of making multicolored microparticles, the microparticles themselves, multiple sets of such microparticles, and multiplexed methods of analyzing a plurality of analytes in a sample are claimed by the instant invention.

A suitable flow cytometer for use with this invention is the Coulter Elite-ESP flow cytometer, or FACScan flow cytometer available from Beckman Coulter, Inc., Fullerton, Calif. Also suitable is the MOFLO flow cytometer available from Cytomation, Inc., Fort Collins, Colo.

In addition to flow cytometry, a centrifuge may be used as the instrument to separate and classify the microparticles. A suitable system is that described in U.S. Pat. No. 5,926,387, incorporated herein by reference.

In addition to flow cytometry and centrifugation, a free-flow electrophoresis apparatus may be used as the instrument to separate and classify the microparticles. A suitable system is that described in U.S. Pat. No. 4,310,408, incorporated herein by reference.

The fluorescent article of the invention can be used for passive or covalent coupling of biological material, i.e., analyte or analytical reactant, such as haptens, antigens, antibodies, enzymes or nucleic acids and used for various types of analyte assays such as immunoassays, nucleic acid (DNA or RNA) assays, affinity purification, cell separation and other medical, diagnostic, and industrial applications.

A large number of protocols exist for detecting the various analytes of interest including proteins of one hundred or more amino acids, peptides of less than one hundred amino acids, polysaccharides, nucleic acids, organic drugs, inorganic drugs, cells, and tissues. The protocols may involve use of a signal producing system, which involves a labeled conjugate, which may be directly or indirectly detected. These techniques may employ dyes, enzymes, enzyme substrates or co-factors, enzyme inhibitors, fluorescers, chemiluminescers, particles, or the like.

Analyte and analyte reactant pairs may, for example, be selected from any of the following combinations, in which either member of the pair may be the analyte and the other the binding partner, e.g., antigen and specific antibody; hormone and hormone receptor; hapten and anti-hapten; polynucleotide and complementary polynucleotide; polynucleotide and polynucleotide binding protein; biotin and avidin or streptavidin; enzyme and enzyme cofactor; and lectin and specific carbohydrate. The term analyte as used hereinafter is a compound or composition to be measured, which is mono- or polyvalent, that is, having one or a plurality of determinant sites, haptenic and antigenic, a single compound or plurality of compounds which share at least one common epitopic or determinant site; or a receptor. The term receptor as used hereinafter is any macromolecular compound or composition capable of recognizing (having an enhanced binding affinity to) a particular spatial and polar organization of a molecule, i.e., epitopic or determinant site. Illustrative receptors include naturally occurring receptors, e.g., thyroxine binding globulin, antibodies, enzymes, immunoglobulin (Fab) fragments, lectins, various proteins found on the surface of cells (cluster of differentiation or CD molecules), and the like. CD molecules denote known and unknown proteins on the surface of eukaryotic cells, e.g., CD4 is the molecule that primarily defines helper T lymphocytes. The term antibody is employed in this case as illustrative of, and to more generally denote receptor. In turn the term ligand is any compound or substance for which a receptor naturally exists or can be prepared.

The haptens may include naturally occurring hormones, naturally occurring drugs, synthetic drugs, pollutants, allergens, affector molecules, growth factors, chemokines, cytokines, lymphokines, amino acids, oligopeptides, chemical intermediates, nucleotides, oligonucleotides or the like. The use for such compounds may be in the detection of drugs of abuse, therapeutic dosage monitoring, health status, donor matching for transplantation purposes, pregnancy (e.g., hCG or alpha-fetoprotein), detection of disease, e.g. endotoxins, cancer antigens, pathogens, and the like. Therapeutic drugs may include, but are not limited to, anti-AIDS substances, anti-cancer substances, antibiotics, anti-viral substances, enzyme inhibitors, neurotoxins, opioids, hypnotics, antihistamines, tranquilizers, anti-convulsants, muscle relaxants and anti-Parkinson substances, antispasmotics and muscle contractants, miotics and anticholinergics, iminunosuppressants (e.g. cyclosporine) anti-glaucoma solutes, anti-parasite and/or anti-protozoal solutes, anti-hypertensives, analgesics, anti-pyretics and anti-inflammatory agents (such as NSAID's), local anesthetics, ophthalmics, prostaglandins, anti-depressants, anti-psychotic substances, anti-emetics, imaging agents, specific targeting agents, neurotransmitters, proteins and cell response modifiers. Proteins are of interest in a wide variety of diagnostics, such as detecting cell populations, blood type, pathogens, immune responses to pathogens, immune complexes, saccharides, lectins, naturally occurring receptors, and the like. Receptors may find use in binding to haptens, proteins, other receptors, or the like, or detection of the presence of pathogens, the level of a particular protein in a physiological fluid, the presence of haptens in a wide variety of samples, such as physiological fluids, air, process streams, water, etc. Nucleic acids may also find use in the detection of complementary strands, proteins specifically binding to nucleic acids, and the like.

The analytical reactants can be also selected among fluorescent reporter molecules capable to react with a variety of inorganic analytes that define properties of biological fluids, air, water, and the like, e.g., $O_2$, $CO_2$, pH, $Ca^{++}$, $Na^+$, $K^+$, or $Cl^-$ as disclosed for example in U.S. Pat. No. 5,747,349 issued to van den Engh et al.

Of particular interest is the binding of microorganisms and cells, including viruses, prokaryotic and eukaryotic cells, unicellular and polycellular organism cells, e.g., fungi, animal, mammal, etc., or fragments thereof. Usually, these large aggregations will be non-covalently bound to the surface through specific binding pair member complexes. By having a high density of binding members bound to the surface, a cell or virus may be complexed by a large number of binding pair members, providing very strong anchoring of the cell, virus, or fragment. The system may then be subjected to vigorous treatment without concern for dislodging the specifically bound entity, while non-specifically bound materials may be readily removed.

The subject of the invention may also be used for detecting pathogens. Monoclonal antibodies may be linked to the surface to serve as catching antibodies. The sample would then be added and cells having the epitope recognized by the antibody would bind to the antibody on the surface. Non-specifically bound pathogens are washed away leaving substantially only specifically bound ones. Labeled monoclonal antibodies are then added which are specific for an epitope other than the epitope recognized by the catching antibody. The term epitope is synonymous to term antigenic determinant and as used herein means a defined domain on the molecule that serves as a reaction or binding site. A molecule may have more than one epitope. For example, first epitope would allow coupling of the analyte with respective analytical reactant and second epitope will provide a binding site or domain for the label reagent. In contrast, a competitor molecule will be interfering (competing) with the formation of a binding pair analyte-analytical reactant. After incubating to allow reaction between the antibodies and pathogens, non-specifically bound antibodies are washed away and the presence of the label determined according to standard detection methods. Pathogens of interest may be viruses such as Herpesviruses, Poxviruses, Togaviruses, Flaviviruses, Picornaviruses, Orthomyxoviruses, Paramyxoviruses, Rhabdoviruses, Coronaviruses, Arenaviruses, and Retroviruses. They may also include bacteria including but not limited to *Escherichia coli, Pseudomonas aeruginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis*, methicillin resistant *Staphylococcus aureus* and *Proteus vulgaris*. The examples of such pathogens are not limited to above pathogens and one skilled in the art will know which specific species of microoragnisms and parasites are of particular importance. The non-exhaustive list of these organisms and associated diseases can be found for example in U.S. Pat. No. 5,795,158 issued to Warinner and incorporated herein by reference.

For detection or quantitation of a target molecule of interest or analyte, a sample is combined with a solution containing the microparticles, the macromolecules on the microparticles are reacted with the analyte, the microparticles are separated from any non-bound components of the sample, and microparticles containing bound molecules are detected by conventional methods. Fluorescently stained microparticles are particularly well suited for flow cytometry analysis in accordance with methods well known to those skilled in the art.

Coating of carrier particles for use in the method of the invention can be effected using, for example, procedures standard in the art. Thus, for example, representative techniques for coating particle systems with antibodies for use in immunoassay procedures are described by Frengen et al. in Clin. Chem. 39 (1993), pp. 2174–2181 and the references contained therein, and by Lindmo et al. in J. Immunol. Methods 126 (1990), pp. 183–189.

Assays using particles of the invention can be carried out in a biological fluid, including separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, and abscesses, and extracts of tissues including biopsies of normal, malignant, and suspect tissues or any other constituents of the body which may contain the analyte of interest. Other similar specimens such as cell or tissue culture or culture broth are also of interest. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products. The test sample can be pre-treated prior to use, such as preparing plasma from blood, diluting viscous fluids, or the like; methods of treatment can involve filtration, distillation, concentration, inactivation of interfering compounds, and the addition of reagents.

A method for detecting multiple subpopulations of analytes of interest in a sample employing a complementary binding moiety to each of said analytes bound to a solid support, wherein each analyte and its complementary binding moiety comprise first and second members of a specific binding pair respectively is provided. The method includes the steps of forming a mixture of known proportions of multiple subpopulations of said complementary binding moieties, wherein each subpopulation comprises a different complementary binding moieties, contacting the sample with the mixture so that specific binding pairs are formed on the solid supports, and relating the presence of analytes of interest in the sample (U.S. Pat. No. 5,567,627 to Lehnen).

For the purposes of the present invention, the label or detectable fluorescent reagent should provide a signal related to the presence of analyte in the sample which results in the detection of electromagnetic radiation, particularly light in the ultra-violet, visible or infrared range.

Assays can be carried out in accordance with the various protocols. In accordance with the subject invention, the sample is contacted with the subject solid substrate and various operations may be carried out, such as the addition of miscellaneous reagents, incubations, washings, and the like. The final result of the assays will be the change in the amount of a product, which absorbs or produces light, either by light absorption or by light emission in relation to the presence or amount of the analyte of interest. Usually, this is as a result of formation of a specific binding complex between complementary members of a specific binding pair, where one of the members may serve as a bridge to form a sandwich (as in "sandwich" assay), or there may be a single complex, or complexes may be bound to complex binding proteins, such as $S.$ $aureus$ protein A, rheumatoid factor, immunoglobulins specific for immune complexes, or the like.

By having fluorescent markers, such as fluorescent particles, fluorescent conjugated antibodies, or the like, the sample may be irradiated with light absorbed by the fluorescers and the emitted light measured by light measuring devices. Dyes can be employed as the label or produced as a result of a reaction, e.g. an enzymatically catalyzed reaction.

Similarly, with nucleic acid assays involving hybridization, one can carry out the necessary steps to determine whether complementary sequences are present, and by employing a wide variety of protocols, provide for a colored or fluorescent label or product of the label, which will indicate the presence or absence of the complementary sequence.

For example, one could activate the surface immediately prior to carrying out the assay by diazotizing the amino functionalities, add the nucleic acid sample to the activated surface, so as to be covalently bound, and then employ probes having a sequence complementary to the sequence of interest and functionalized, for example, by having a biotin label. After completion of the hybridization step, one could add enzyme or fluorochrome conjugated to avidin, which would bind to any biotin bound to the surface through hybridization. After washing away non-specifically bound avidin, the fluorochrome can be measured directly or the substrate for the enzyme could be added and the formation of product would be indicative of the presence and amount of the complementary sequence.

A variation would be to employ an antigen recognized by a cell receptor. The antigen would be bound to the surface to catch the cells and a labeled antigen used to label the cells. The receptor could be surface immunoglobulin. In this way the presence of the specifically bound cells could be determined, whereby having the antigen of interest complementary to the receptor bound to the surface, cells having the specific immunoglobulin for such antigen could be determined. Instead of having antigen, one would have antibodies to the antigen bound to the surface to non-covalently bind the antigen to the surface.

The subject article may also find use in isolating various products of interest, such as blood plasma proteins, growth factors, clotting factors, anti-clotting factors, or the like, which may then be released from the complex by various salt solutions. The article of the invention may be used for a variety of other purposes, whenever one wishes to provide a high density of oriented molecules at a surface or visualize events or provide for ready transmission of light, where the analyte substance is non-diffusively bound to a solid surface.

EXAMPLE 1

General Outline of the Fluorescent Staining of Particles

A 1% of stock of nanospheres (300 nm polystyrene, amino functionalized) in an aqueous medium is pipetted onto a round bottom flask. Next, a dye solution (composed of one or more dyes) in an organic solvent, such as chloroform is added. The suspension is allowed to sit for until the dye solution is no longer absorbed by nanospheres. The solvent is removed under reduced pressure (vacuum pump). An aqueous medium is added to stained nanospheres, sonicated and transferred to a storage container.

In one embodiment of the invention, one or more sets of nanoparticles are prepared, each set stained with a distinct dye at a predetermined concentration. In yet another embodiment of the invention the carrier microspheres themselves are stained with one or more fluorescent dyes.

The sets of monochromic nanoparticles are then mixed at a desired ratio and used further for attaching or conjugating them to a preparation of carrier microspheres. This construction is the article of the invention. The resulting fluorescent articles are then tested to determine the fluorescence activity/intensity of the preparation. Each set or population of nanoparticle-microparticle conjugates displays an optical pattern or fluorescent signal (an "optical signature") which is unique to the specific set or population of articles. Another population of articles may for example have the same total number of fluorescent nanoparticles but they are mixed at different ratio. Thus by having only two dyes one can prepare a high number of sets of article with unique fluorescent signal. By having the preparation of microparticles stained with yet another dye one obtains even higher number of multicolored articles. This is a significant improvement over the prior art. The present inventors were able, for the first time, to reduce to practice the invention.

EXAMPLE 2

Staining With Two Dyes Simultaneously

A single solution containing two different dyes is prepared and used to stain the same particle. One dye is a red fluorescent dye 1,3-bis [(1,3-dihydro-1,3,3-trimethyl-2H-indol-2-ylidene)methyl]-2,4-dihydroxy-cyclobutenediylium, bis(inner salt) and second dye is orange fluorescent dye can be 2-(3,5-dimethylpyrrol-2-yl)-4-(3,5-dimethyl-2H-pyrrol-2-ylidene)-3-hydroxy-2-cyclobuten-1-one. The peak emission of dye #1 is 585 nm, and the peak emission of dye #2 is 630 nm. These dyes are chosen because they fall in the center of two of the fluorescence channels of a Becton Dickinson FACScan flow cytometer, which is the measurement device used. The choice of fluorescence channels is, however, relative and immaterial since another flow cytometry apparatus may have different settings.

By having the preparation of microparticles or nanoparticles stained with two dyes mixed at different ratios one obtains even higher number of multicolored articles than disclosed in Example 1.

EXAMPLE 3

Preparation of Multiple Sets or Populations of Distinct Populations of Particles While theoretically it has been speculated that such sets can be extremely valuable for multiplex analysis (see for example McHugh, "Flow Microsphere Immunoassay for the Quantitative and Simultaneous Detection of Multiple Soluble Analytes," in Methods in Cell Biology, 42, Part B, (Academic Press, 1994) so far there are no known examples in the art enabling and demonstrating the reduction to practice of tangible, multicolored beads. At best only 1 and perhaps a maximum of 5 population of beads containing various ratios of two dyes could have been possible. For example, U.S. Pat. No. 4,717,655 discloses such beads, however, the disclosure was not enabled and the composition matter as well as the method of preparing such beads is unrelated to the instant invention. In contrast, due to the instant invention it is now technically possible to obtain truly distinct multiple subsets.

To make another population of beads with different fluorescent characteristics the ratio of nanoparticle populations with red/orange dyes is altered by an adequate increment in proportion so that obtained ratio optically does not overlap with the former ratio. The instant invention provides a very high number of sets of optically distinct carrier beads by varying the ratio of just 2 populations of nanoparticles stained with 2 distinct dyes. This example is not in any way a limiting one since one of ordinary skill may easily generate smaller or higher number of bead subsets by using the instant teaching. One can also use only one population of nanobeads and vary the ratio to carrier particle, which is also stained. One skilled in the art may appreciate that nothing even close to this achievement has ever been enabled in the actual practice. The prior art failed to teach one of ordinary skill how to arrive at that.

EXAMPLE 4

Coupling of a Fluorescent Dye to an Antibody

Fluorescent dye 5(6)-carboxyfluorescein is associated with the antibody by use of 5(6)-carboxyfluorescein-N-hydroxysuccinimide ester. To prepare the ester, N-hydroxysuccinimide (2.1 mM) and dicyclohexylcarbodiimide (2.1 mM) are added to 5(6)-carboxy fluorescein (2.0 mM) dissolved in tetrahydrofuran. The resulting reaction mixture is left in the cold 4° C. for three days to allow formation of the ester. 5(6)-carboxyfluorescein-N-hydroxysuccinimide ester is then reacted with purified primary antibody IgG (10 mg) dissolved in 0.1M $NaHCO_3$ (3 ml; pH 8.6) containing 0.1M NaCl. The resulting fluorescein labeled primary antibody is then purified known methods in the art such as gel filtration.

EXAMPLE 5

Coupling of an Analytical Reactant to Microparticles and/or Nanoparticles

A series of antibodies, antigens, or nucleic acid probes, collectively named hereinafter as analytical reactants, are bound to the beads by any of a number of conventional procedures as described by Colvin et al., "The Covalent Binding of Enzymes and Immunoglobulins to Hydrophilic Microspheres" in Microspheres: Medical and Biological Applications, 1–13, CRC, Boca Raton, Fla., 1988; Cantarero et al., "The Adsorptive Characteristics of Proteins for Polystyrene and Their Significance in Solid-Phase Immunoassays," Anal Biochem, 105, 375–382 (1980); and Illum et al., "Attachment of Monoclonal Antibodies to Microspheres," Methods in Enzymol, 112, 67–84 (1985) 112, 67–84 (1985).

In this example a rabbit antibody raised against an analyte is coupled to the microparticles. Antibody is dialyzed into phosphate buffered saline (PBS), pH 8, resulting in a concentration of about 3 mg/ml as determined by absorbance at 280 nm. Six mg of antibody is derivatized with SPDP (3-(2-pyridyldithio propionic acid N-hydroxysuccinimide ester, Sigma Chemical Co., St. Louis, Mo.) for 30 min. using a solution of 1.5 mg SPDP in 1.5 ml methanol. 1M sodium acetate, pH 4.5 is then added and followed by 1M dithiothreitol (DTT). The solution is stirred at room temperature for an additional 30 min., then applied to a SEPHADEX G-25 column (Pharmacia LKB Biotechnology, Inc.) to remove free DTT and place the derivatized antibody into pH 8 coupling buffer (50 mM Tris Base, 50 mM sodium acetate, 50 mM sodium chloride and 1 mM EDTA). The antibody preparation is mixed with the microparticles, which are brought to pH 8 with Tris immediately before use, at a ratio of 1 mg antibody per 100 nM maleimide. The mixture is incubated for 2 hours. The functionalized particles are then separated from free antibody on a SEPHAROSE column (Pharmacia LKB Biotechnology, Inc.) equilibrated in 30 mM MOPSO, 10 mM EDTA, 100 mM glucose, and 0.2% sodium azide, pH 6.8. Miles Pentex Fraction V BSA is added to give a final w/v concentration of 1%. Other proteins and amine-containing compounds, such as enzymes, avidin, biotin or polysaccharides, can be covalently linked to various particles by using above or similar standard techniques well known in the art.

After attachment of a reactant to the beads' surface, aliquots from each subset are mixed to create a pool containing known amounts of beads within each subset. Preferably, the pooled set is prepared with equal volumes of beads from each subset, so that the set contains about the same number of beads from each subset or population. This pool is then incubated with a fluid sample of interest, such as serum or plasma, to test for the presence of antigens (analytes) in the fluid that are reactive with antibodies on the beads. Such incubation is generally performed under conditions of temperature, pH, ionic concentrations, and the like that facilitate specific reaction of analytical reactant in the fluid sample with analyte on the bead surface. After a sufficient period of time, the beads in the mixture are incubated for another period of time with a "label reagent" such as for example, fluorescein-labeled goat antibody that binds the analyte of interest via an epitope (antibody-binding fragment of the analyte) that is different from the binding epitope of the rabbit antibody. The secondary antibody or label reagent will bind to the analyte of interest, which is bound to the beads via capturing rabbit antibody. After washing (or without washing), the beads are processed by a flow cytometer and the four classification parameters forward light scatter, side light scatter, red fluorescence, and orange fluorescence are measured and used to identify the subset or population to which each bead belongs. A simultaneous measurement of green fluorescence (measurement parameter associated with the label reagent) for each bead allows one to determine whether the bead has antibody bound to it. Because the subset to which a bead belongs is correlated with the presence of a particular antigen, e.g., series of grass allergens, various substance abuse drugs, set of pathogens, one may readily determine the specificity of the antibody bound to a bead as a function of the subset to which it belongs.

Grass allergens may include ragweed and mixed-grass pollen extracts (timothy, orchard, June and meadow grass). Samples of these grass allergens which may serve for calibration and comparative studies as a reference material can be purchased from Greer Laboratories (Lenoir, N.C.). Specific examples of drugs of abuse and controlled substances, may include but are not intended to be limited to, amphetamine; ethamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methapualone; opiates such as heroin, morphine, codeine, hydromorphone, hydrocodone, methadone, oxycodone, oxymorphone and opium; phencyclidine; propoxyhene; and the like. These substances can serve as analytes of interest and as reference material as well.

EXAMPLE 6

Carbodiimide Attachment

This example discloses a method of attaching an analyte, e.g., an antibody, to a particle using known carbodiimide chemistry. Note that this same method is used not only for attaching a particular analyte but also for attaching nanoparticles to the carrier microparticle particle.

A monoclonal antibody is covalently attached to polymeric particles having pendant carboxyl groups on the outer surfaces. The particles are composed of poly(styrene-co-methacrylic acid) (90:10 molar ratio). A sample of the polymeric particles (30 mg dry weight) is mixed with the carbodiimide, followed by the addition of 1.5 mg of antibody. The attachment reactions are carried out by incubation of the mixtures for 24 hours with rotation at room temperature. The reaction is stopped by the addition of bovine serum albumin (30 mg/ml), and incubation is then continued for an additional four hours. The reaction mixtures are centrifuged, the supernatant discarded, and the pellets washed once with phosphate buffered saline solution (pH 7.4), and then resuspended in the saline solution. The mass of antibody bound to each latex preparation is determined by assaying the number of radioactive counts for samples run in parallel having tritiated bovine gamma globulin bound to the particles. The covalent/total ratio is calculated following incubation with sodium dodecylsulfate surfactant. The further details regarding this technique can be found for example in U.S. Pat. No. 5,397,695 to Sutton, et al.

The nanoparticles are covalently attached to the carrier microparticles in essentially similar manner as above. Obtained coupled particles can be further coated by a polymeric shell, which is, for example, formed by mixing the particles in monomeric styrene (0% to 80%) and divinyl benzene (20% to 100%) for a time sufficient to coat the particles and then polymerize the coat by adding potassium persulfate. Another way of obtaining the shell is to cross-link together surface functional groups by a multivalent molecule. For example, 1,1,1-tris(aminoethyl)propionitrile caps at least three carboxylic acid moieties on the surface of the particles. The shell surface is further modified to provide respective functional groups by oxidizing the nitrile group to a carboxylic acid or reducing it to an amine.

EXAMPLE 7

Preparation of FITC-labeled Albumin Microparticles

Carrier microparticles can be made of any polymeric material including proteinaceous material. This example describes the method of fluorescently staining such a carrier particle. Fluorescein isothiocyanate (FITC, Sigma Chemical Company, St. Louis, Mo.) is conjugated to human serum albumin (HSA) in the presence of polymers causing the formation of conjugate particles. Free FITC is washed away from the particles, and the particles redissolved in NaOH yielding FITC-labeled HSA in the absence of free FITC.

FITC (6.2 $\mu$g) is dissolved in 2 ml of carbonate buffer (pH 10). The dissolved FITC is combined with 1 ml of HSA (25%) and 6 ml of a polymer solution containing 25% PVP and 25% PEG is added in 0.1M sodium acetate pH 5.0, while vortexing. The mixture is incubated sequentially at room temperature, 37° C., and 58° C. for 30 minutes each. Conjugate particles are formed as a result. The mixture is centrifuged in a microfuge at 14,000 rpm, the supernatant removed, and the particles washed three times with deionized water (10 ml each). The particles are resuspended in 10 ml deionized water. The resuspended particles are visualized in a fluorescence microscope. All fluorescence is associated with the particles. No free fluorescence is observed, indicating that all of the FITC is conjugated to albumin and there are no free FITC molecules.

EXAMPLE 8

Formation of Microparticles With Attached Oligonucleotide Probe

In a first step, a suitable probe for detecting a DNA sequence of interest is selected. Such a probe is coupled to particles by techniques known in the art, (e.g., carbodiimide coupling see above, or other means) to produce individual aliquots of beads having known oligonucleotides coupled thereto. The oligonucleotides must be a sufficient length to allow specific hybridization in the assay, e.g., generally between about 5 and 500 nucleotides, preferably between about 10 and 50 nucleotides, more preferably between about 20 and 30 nucleotides in length. In a preferred embodiment, a saturating amount of the oligonucleotide is bound to the bead. Fluorescent oligonucleotides, complementary to all or part of the sequences attached to each bead, are also prepared. Next, PCR primers are selected which are used to amplify the particular region of DNA in the sample that contains the sequence corresponding to the oligonucleotide coupled to the beads. Either double stranded (ds) or single stranded (ss) PCR techniques may be used. If double stranded product (dsDNA) is produced, the amplified PCR product is made single stranded by heating to a sufficient temperature to and for a sufficient time to denature the dsDNA according to well-known methods in the art. The mixture is cooled, and the beads are added and incubated with the PCR product under conditions suitable to allow hybridization to occur between the oligonucleotide on the particles and the PCR product (e.g., at room temperature for about 10 minutes). The hybridization time may vary depending on desired results and can last for example as long as 24 hours or longer. The fluorescent DNA probe is then added and the entire mixture incubated under hybridization conditions suitable to allow competitive hybridization to occur. As those of skill in the art will recognize, the concentrations of the PCR product and fluorescent probe to be used may vary and may be adjusted to optimize the reaction. It is also recognized that the order of mixing probe, target, and competitor molecule may vary and not necessarily the same as described herein.

In general, the concentrations of PCR product and fluorescent probe to be used are adjusted so as to optimize the detectable loss of fluorescence resulting from competitive inhibition without sacrificing the ability of the assay to discriminate between perfect complementarity and one or more nucleotide mismatches. One may deliberately create mismatches as in degenerate probe assays. In an exemplary assay, the concentration of PCR product complementary to the oligonucleotide bound to the beads is in the order of 1 to 10 times the concentration of fluorescent probe used. If the PCR product is much longer than the bead bound oligonucleotide, the amount of PCR product is increased accordingly to reflect relative molar concentrations in the region of DNA complementary to bead bound oligonucleotide. The fluorescent probe is preferably added in an amount sufficient to saturate the complementary oligonucleotide on the beads, e.g., in the range of from about 1 to 1000 fold and more preferably 2–100 fold or more preferably about 20–50 fold the concentration of oligonucleotide bound to the bead.

The fluorescent oligonucleotide probe may be prepared by methods known in the art such as those described in U.S. Pat. No. 5,403,711, which is incorporated herein by reference, or by other means well-known in the art.

EXAMPLE 9

Displacement or Competition Assay Using a Competitor Molecule

Assays for many substances in a clinical laboratory are based on the interference with specific ligand-ligate or antigen-antibody interactions. In these assays, one member of the ligand-ligate pair is labeled with the fluorophore or fluorochrome and one member is immobilized on the beads. Soluble, unlabeled analyte, which may be ligand or ligate, is added to the reaction mixture to competitively inhibit interaction of the labeled component with the immobilized component. It is usually not important which member of the pair is labeled and which is immobilized; however, in certain assays, functional advantages may dictate the orientation of the assay or sequence of order upon which the ingredients are admixed.

In an exemplary assay of this type, each bead subset is provided with an antigen. The anti-gencoated beads are then reacted with labeled antibody specific for the antigen on the bead surface. Subsequent addition of a test fluid containing soluble analyte (inhibitor) will displace the labeled antibody from the beads in direct proportion to the concentration of the soluble analyte. A standard curve of known analyte concentrations is used to provide accurate quantification of analyte in the test sample. For the purposes of clarity an analyte of known concentration that is used for building a standard curve is referred to as a reference material. The reference material is usually and essentially identical to the analyte or part of the analyte molecule.

If the PCR product is perfectly complementary to the oligonucleotide on the bead, it will competitively hybridize to it with a higher degree of binding affinity than will be observed if the PCR product is not perfectly complementary. Thus, the PCR product decreases the binding of the fluorescent complementary oligonucleotide to the bead more or less efficiently depending on the level of complementarity of the PCR product.

EXAMPLE 10

Nucleic Acid Analysis

Nucleic acid used for this assay is either naturally occurring nucleic acid such as found in an unmodified specimen, e.g., blood cell or pathogen, or alternatively it can be an amplified nucleic acid such as resulting from a cloning of a plasmid or obtained as a result of polymerase chain reaction (PCR).

The power and sensitivity of PCR found its application to a wide variety of analytical problems in which detection of DNA or RNA oligonucleotide sequences is required. One major difficulty with the PCR technique is the cumbersome nature of the methods of measuring and analyzing the endproduct, i.e., amplified DNA. A flow cytometric bead-based hybridization assay permits the extremely rapid and accurate detection of genetic sequences of interest. In a preferred embodiment of this invention, a bead to which a nucleic acid segment of interest has been coupled is provided. A PCR product of interest (or any other DNA or cDNA segment not necessarily obtained by PCR procedure) is detected by virtue of its ability to competitively inhibit hybridization between the nucleic acid segment on the bead and a complementary fluorescent DNA probe. The method is sensitive and precise and allows the detection of single point mutations in the PCR product or DNA of interest. The multiplexed DNA analysis method can be applied to detect any PCR product or other DNA of interest for specific polymorphisms or mutations and one skilled in the art will recognize that numerous applications can be imagined such as presence of histocompatibility alleles associated with susceptibility to diseases, mutations associated with genetic diseases, autoimmune diseases, or mutations of oncogenes or genes associated with neoplasia or risk of neoplasia. Several genes associated with above named conditions are now known including but not limited to cystic fibrosis gene, multiple endocrine neoplasia type 2a (MEN2a), multiple endocrine neoplasia type 2b (MEN2b), multiple endocrine neoplasia type 1 (MEN 1), ret proto-oncogene, low density lipoprotein (LDL) receptor, neurofibromatosis type 1 (NF1), neurofibromatosis type 2 (NF2), breast and ovarian cancer susceptibility type 1 (BRCA1), breast and ovarian cancer susceptibility type 2 (BRCA2), breast and ovarian cancer susceptibility type 3 (BRCA3), adenomatous polyposis coli (APC), adenosine deaminase, xeroderma pigmentosum group A correcting gene (XPAC), excision repair cross complementing rodent repair deficiency complementation group 6 (ERCC6), fragile X mental retardation protein 1 (fmr1), Duchenne muscular dystrophy gene, myotonic dystrophy protein kinase, androgen receptor, Huntington's disease associated gene, hypoxanthine-guanine phosphoribotransferase (HPRT), apolipoprotein E, beta-hexosaminidase alpha chain (HEXA), steroid 21-hydroxylase, angiotensin, human nodular mixed lymphocytic and histiocytic cell mismatch repair (hNMLH 1 and 2), retinoblastoma susceptibility (Rb), transformation-associated protein 53 (p53), ras, breakpoint cluster region/tyrosine-protein kinase (bcr/abl), B-cell leukemia/lymphoma 2 (bcl-2), genes encoding ion transporters, and combination thereof. These genes may or may not be associated with diseases and clinical disorders selected from the group consisting of human myotonia, paramyotonia congenita, hyperkalemic periodic paralysis, hypertrophic cardiomyopathy, hereditary ovalocytic red blood cells, hereditary spherocytosis, glucose/galactose malabsorption, familial hypercholesterolemia, tuberous sclerosis, severe combined immunodeficiency, autoimmune disease, insulin-dependent diabetes mellitus, Cockayne's syndrome, spinal and bulbar muscular atrophy, Peutz-Jegher's syndrome, Lesh-Nyhan syndrome, Tay-Sachs disease, Alzheimer's disease, congenital adrenal hyperplasia and hypertension, essential hypertension, hereditary non-polyposis colon cancer, hereditary colon cancer, colon cancer, familial retinoblastoma, Li-Fraumeni syndrome, chronic myelogenous leukemia, follicular and diffuse lymphoma, malignant lymphoma, leukemia, skin cancer, lung cancer, pancreatic cancer, and combination thereof.

In addition to above named malignancies other types of cancer may comprise fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, or myeloma.

In a same way mutated or wild type (non-mutated) nucleic acid segments from pathogenic organisms such as bacterial, viral, fungal, mycoplasmal, rickettsial, chlamydial, or protozoan pathogens are detected simultaneously.

EXAMPLE 11

Enzyme Assays

The invention is also useful for measurement of enzymes, enzyme inhibitors, enzyme substrates, enzyme metabolites such as lactate, ATP, glucose and other related diagnostically significant analytes. For example, bead subsets are generated with selected fluorescent substrates, which are enzymatically cleaved from the bead, resulting in a loss of fluorescence. Enzymes that can be detected and measured using the instant invention include but are not restricted to, proteases, hydrolases, oxidoreductases, transferases, lyases, ligases, synthetases, isomerases, glycosidases, and nucleotidases. Any enzyme that results in selected bond cleavage can be measured. Alternatively, the action of the enzyme on the bead-bound substrate results in the formation or identification of a binding pair (ligate) for a fluorescent ligand present in the reaction mixture. The bead bearing the modified substrate then becomes fluorescent by virtue of binding of the fluorescent ligand to the newly formed ligate. Because each type of bead bearing the unique substrate can be distinguished, a mixture of bead subsets is used to measure several enzyme activities simultaneously in the same reaction mixture.

Enzyme inhibitors are substances, which inhibit an enzymatic reaction. Many of them are significant in clinical application. Examples of enzyme inhibitors include edrophonium chloride, N-methylphysostigmine, neostigmine bromide, physostigmine sulfate, tacrine, tacrine 1-hydroxy maleate, iodotubercidin, p-bromotetramisole, 10-(a-diethylaminopropionyl)-phenothiazine, calmidazolium, hemicholinium-3,3,5-dinitrocatechol, diacylglycerol kinase inhibitor I, diacylglycerol kinase inhibitor II, 3-phenylpropargylaminie, N-monomethyl-L-arginine, carbidopa, 3-hydroxybenzylhydrazine, hydralazine, clorgyline, deprenyl hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvaleratehydrochloride, 3-isobutyl-1-methylxanthne, papaverine, indomethacin, 2-cyclooctyl-2-hydroxyethylamine, 2,3-dichloro-a-methylbenzylamine (DCMB), 8,9-dichloro-2,3,4,5-tetrahydro-1H-2-benzazepine, p-aminoglutethimide, p-aminoglutethimide tartrate, p-aminoglutethimide tartrate, 3-iodotyrosine, alpha-methyltyrosine,L-, alpha-methyltyrosine, L-, acetazolamide, dichlorphenamide, 6-hydroxy-2-benzothiazolesulfonamide, and allopurinol.

EXAMPLE 12

Single Analyte, Multiple Sample Sources

In this example, multiple samples from multiple sources, for example, sera from a number of clinical patients, are assayed for a single analyte in this example the human thyroid hormone thyroxine. The process of EXAMPLE 1 and 3 is used to prepare a number of sets or populations or subpopulations of nanoparticle-microparticle conjugates each of which have a distinct optical pattern or fluorescent signature. The number of different sets or populations or subpopulations of conjugates must equal the number of samples plus the necessary controls for the assay. In the present example, there are 10 samples plus 4 controls which requires 14 sets of conjugates. In this example, 14 levels or concentrations of each dye are used.

The sets of conjugates in this example are stained as in EXAMPLE 2. In this case the emission peak of dye #1 is 585 nm (red fluorescence) and the peak emission of dye #2 is 630 nm (orange fluorescence). A Becton Dickinson FACScan flow cytometer is the instrument used to assay the particles.

The 14 subpopulations of microparticles in this example are each uniquely labeled with one of 14 levels of concentrations of dye #1 and one of 14 levels or concentrations of dye #2, allowing the unique identification of each microparticles of each of the subpopulations using the flow cytometer.

The thyroxine concentration of each sample is determined using a sandwich assay. Antibodies against thyroxine are raised in rabbits and are coupled to the microparticles and assayed using the methods of EXAMPLE 5. Each subpopulation of microparticles is coupled with the same preparation of rabbit thyroxine antibodies. Each subpopulation is placed in a container such as a tube or microtiter plate, mixed with a different clinical sample or control, and incubated for 10 minutes at room temperature. This allows any thyroxine in the sample to bind to the rabbit antibody which is attached to the microparticles. A secondary antibody or reagent which is labeled with a fluorescent dye having a fluorescent emission peak different from dye #1 and dye #2 is then added to the microparticles. For example, a goat antibody which also reacts with the analyte is labeled with dye #3 fluorescent (green fluorescence) and is allowed to react with the microparticles for 10 minutes at room temperature. The microparticles are washed with water to remove unbound goat antibody, and all samples of microparticles are removed from the container using a multichannel micropipetter, combined into a single tube, and passed through a flow cytometer. In this example, red fluorescence and orange fluorescence is measured and used to identify which subpopulation of which each microparticle is a member, and thereby which clinical sample is associated with each microparticle. The average amount of green fluorescence associated with each microparticle allows the determination of the amount of thyroxin in each sample.

The above method is especially advantageous because it is possible to combine all samples and run them all at once through the flow cytometer. There is no requirement that samples be examined individually. This provides a significant increase in the through-put of a flow cytometer, an expensive instrument.

EXAMPLE 13

Single Sample Source, Multiple Analytes

In another configuration the invention is used to determine the concentration of several different analytes in a single sample. A single clinical serum sample can be assayed for 6 different iodine-containing organic compounds of the thyroid gland as analytes.

Unique subpopulations of microparticles are obtained as in EXAMPLE 12. Rabbit antibodies are raised against the following compounds: a. 3,5-diiodotyrosine; b. thyroxine; c. 3,5,3'-triiodothyronine; d. 3,3',5'-triiodothyronine; e. 3,3'-diiodothyronine, and f. 3-monoiodotyrosine. Each antibody is coupled with a unique subpopulation of microparticles as in EXAMPLE 12. Each subpopulation of microparticles which now bear a single coupled antibody is mixed with an aliquot of the serum sample and incubated as in EXAMPLE 12. This allows any of the analytes a.-f. present in the serum sample to bind to the microparticles of the appropriate subpopulation. Each sample treated with the corresponding goat antibody which bears dye #3 (green fluorescence) and which binds to analyte a.-f. as in EXAMPLE 12. For example, the sample in which rabbit antibody against thyroxine is allowed to react with an aliquot of the sample and then is treated with a goat antibody against thyroxine which is stained with dye #3. The samples are combined and analyzed using the flow cytometer.

It is easy to see how more than one patient's serum sample can be analyzed using this procedure. It is necessary only that there is a unique subpopulation of microparticles for each sample/analyte combination. It should also be noted that the same dye #3 may be used for the several different goat antibodies in this example.

Again, there it is possible to combine the subpopulations of microparticles before they are analyzed with the flow cytometer, thereby obtaining major savings in time and labor and increasing the through-put of the flow cytometer.

The above examples are used to illustrate and perform most common immunodiagnostic, enzyme, drugs, and/or nucleic acid assays. It is important to note that both cell and soluble analyte assays may be performed. Other applications such as high throughput screening of combinatorial chemistry libraries for discovering new drugs, environmental screening of pollutants, drug testing, food safety-related investigations, testing of multiple analytes for agricultural needs, etc, can be imagined and carried out according to standard procedures known in the art.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

What is claimed is:

1. A carrier particle comprising a polymeric microparticle and at least one nanoparticle of at least one nanoparticle population coupled with said polymeic microparticle, wherein said at least one nanoparticle has a diameter in the range of 10–1,000 nm.

2. The carrier particle of claim 1 wherein at least one nanoparticle of said at least one nanoparticle population includes a surface which allows attachment of functional groups thereto.

3. A carrier particle comprising a polymeric microparticle wherein said polymeric microparticle includes a plurality of nanoparticles of at least one nanoparticle population coupled with said polymeric microparticle.

4. The carrier particle of claim 3 wherein said microparticle includes a plurality of nanoparticles of at least two nanoparticle populations coupled with said microparticle.

5. The carrier particle of claim 4 wherein said nanoparticles of said at least two nanoparticle populations are stained with different dyes.

6. The carrier particle of claim 5 wherein said different dyes are different fluorescent dyes.

7. The carrier particle of claim 4 wherein said nanoparticles of said at least two nanoparticle populations are stained with different dye concentrations.

8. A carrier particle comprising a microparticle and at least one nanoparticle of at least one nanoparticle population coupled with said microparticle wherein said nanoparticles in said at least one nanoparticle population are dyed with the same concentration of a dye.

9. The carrier particle of claim 8 wherein the dye is a fluorescent dye.

10. A carrier particle comprising a microparticle and at least one nanoparticle of at least one nanoparticle population coupled with said microparticle wherein said microparticle is stained with a dye.

11. The carrier particle of claim 10 wherein said dye is a fluorescent dye.

12. A plurality of carrier particles which include microparticles having nanoparticles of more than one nanoparticle population coupled with said microparticles.

13. The plurality of microparticles of claim 12 which include microparticles having nanoparticles of one nanoparticle population coupled with said microparticles and which include microparticles having nanoparticles of another nanoparticle population coupled with said microparticles.

14. A method of determining concentration of an analyte in a sample comprising the steps of:
  (a) providing a population of carrier particles which includes microparticles coupled with a subpopulation of nanoparticles, thereby providing a subpopulation of carrier particles, the subpopulation of nanoparticles being labeled so as to provide a specific subpopulation characteristic detectable by an instrument, the carrier particles of the specific carrier particle subpopulation having attached thereto a reagent which reacts with the analyte to form a bimolecular product,
  (b) contacting the sample with the population of carrier particles,
  (c) identifying the subpopulation of the carrier particles using the specific subpopulation characteristic, and
  (d) calculating the concentration of the analyte in the sample according to the bimolecular product detected for the subpopulation of carrier particles.

15. The method of claim 14 wherein the subpopulation of nanoparticles is labeled with a fluorescent label.

16. A method of determining concentration of a multiplicity of specific analytes in a sample comprising the steps of:
  (a) providing a population of carrier particles which includes microparticles coupled with a multiplicity of subpopulations of nanoparticles, thereby providing a multiplicity of subpopulations of carrier particles, each subpopulation of nanoparticles being labeled so as to provide a specific subpopulation characteristic detectable by an instrument, the carrier particles of a specific carrier particle subpopulation having attached thereto a specific reagent which reacts with a specific analyte to form a specific bimolecular product,
  (b) contacting the sample containing the multiplicity of specific analytes with the population of carrier particles,
  (c) identifying the multiplicity of subpopulations of the carrier particles using the specific subpopulation characteristics, and
  (d) calculating the concentrations of the specific analytes in the sample according to the specific bimolecular product detected for each subpopulation of carrier particle.

17. The method of claim 16 wherein each subpopulation of nanoparticles is labeled with a specific fluorescent label.

18. The method of claim 16 wherein the instrument is a flow cytometer.

19. The method of claim 16 wherein the instrument is an electrophoresis cell.

20. The method of claim 16 wherein the instrument is a centrifuge.

21. The method of claim 16 wherein a specific characteristic detectable by the instrument is a fluorescence emission characteristic.

22. The method of claim 16 wherein a specific characteristic detectable by the instrument is a radioactive emission characteristic.

23. The method of claim 16 wherein a specific characteristic detectable by the instrument is a carrier particle size characteristic.

24. The method of claim 16 wherein a specific characteristic detectable by the instrument is a carrier particle density characteristic.

25. The method of claim 16 wherein a specific characteristic detectable by the instrument is a carrier particle color characteristic.

26. The method of claim 16 wherein a specific characteristic detectable by the instrument is an electrical charge characteristic of a carrier particle.

27. The method of claim 16 wherein a specific characteristic detectable by the instrument is a magnetic charge characteristic of a carrier particle.

28. The method of claim 16 wherein the bimolecular product includes strands of DNA.

29. The method of claim 16 wherein the bimolecular product includes an antibody and an antigen.

30. The method of claim 16 wherein the bimolecular product includes a receptor and a ligand.

31. The method of claim 16 wherein the bimolecular product includes a reaction product of an enzyme and an enzyme substrate.

32. A kit for the detection of an analyte of interest, the kit comprising at least one polymeric microparticle with attached nanoparticles and at least one analytical reagent.

33. A kit according to claim 32 wherein said kit further comprises a secondary reagent and a standard reagent.

34. A kit according to claim 32 wherein said analytical reagent is capable of binding to an analyte.

35. A kit according to claim 32 wherein said nanoparticles contain a fluorescent label.

36. A kit according to claim 32 which includes nanoparticles containing a fluorescent label coupled with said microparticle, a quantity of competitor molecule, and a quantity reference material.

37. A kit according to claim 32 further including a wash buffer.

38. A kit according to claim 32 further including a container for carrying out a bimolecular reaction.

* * * * *

UNITED STATES PATENT AND TRADEMARK OFFICE
CERTIFICATE OF CORRECTION

PATENT NO.   : 6,649,414 B1
DATED        : November 18, 2003
INVENTOR(S)  : Chandler et al.

It is certified that error appears in the above-identified patent and that said Letters Patent is hereby corrected as shown below:

Title page,
Item [56], References Cited, U.S. PATENT DOCUMENTS, please add:

-- 4,987,539    01/22/1991    MOORE et al.
       5,093,234    03/03/1992    SCHWARTZ
       5,326,692    07/05/1994    BRINKLEY et al.
       5,786,219    07/28/1998    ZHANG et al.
       5,872,015    02/16/1999    VENTON et al. --

FOREIGN PATENT DOCUMENTS, please add:

-- WO    97/20074    06/05/1997
       WO    99/01577    07/14/1999
       WO    99/37814    /7/29/1999 --

OTHER PUBLICATIONS, please add:

-- McHUGH, T.M. "Method in Cell Biology, 2nd Ed. Part B, Flow Microspher Immunoassay for the Quantitative and Simultaneous Detection of Multiple Soluble Analytes. 1984, Vol. 42, Chapter 33, pages 575-594.

PHAN, QUANG N., International Search Report for PCT/US99/01315, April 7, 1999.

ZINNGREBE, U. International Search Report for PCT/US00/22543, October 25, 2000. --

Signed and Sealed this

Twenty-fourth Day of August, 2004

JON W. DUDAS
*Director of the United States Patent and Trademark Office*